United States Patent
Hori et al.

(10) Patent No.: US 11,058,610 B2
(45) Date of Patent: Jul. 13, 2021

(54) AGENT FOR TREATING POWDER FOR COSMETIC, POWDER FOR COSMETIC, AND COSMETIC FORMULATED USING SAID POWDER

(71) Applicant: Dow Corning Toray Co., Ltd., Tokyo (JP)

(72) Inventors: Seiji Hori, Chiba (JP); Yasue Kanzaki, Chiba (JP); Sayuri Kikunaga, Chiba (JP); Norihisa Kishimoto, Chiba (JP)

(73) Assignee: Dow Toray Co., Ltd., Tokyo (JP)

( * ) Notice: Subject to any disclaimer, the term of this patent is extended or adjusted under 35 U.S.C. 154(b) by 0 days.

(21) Appl. No.: 16/311,425

(22) PCT Filed: Jun. 20, 2017

(86) PCT No.: PCT/JP2017/022734
§ 371 (c)(1),
(2) Date: Jan. 14, 2019

(87) PCT Pub. No.: WO2017/221940
PCT Pub. Date: Dec. 28, 2017

(65) Prior Publication Data
US 2019/0192387 A1    Jun. 27, 2019

(30) Foreign Application Priority Data

Jun. 24, 2016  (JP) .............................. JP2016-125665

(51) Int. Cl.
*A61K 8/02* (2006.01)
*A61K 8/29* (2006.01)
*A61Q 17/04* (2006.01)
*A61K 8/06* (2006.01)

(52) U.S. Cl.
CPC .............. *A61K 8/022* (2013.01); *A61K 8/29* (2013.01); *A61Q 17/04* (2013.01); *A61K 8/064* (2013.01); *A61K 2800/412* (2013.01); *A61K 2800/614* (2013.01)

(58) Field of Classification Search
CPC .......... A61K 8/022; A61K 8/29; A61K 8/064; A61K 2800/412; A61K 2800/614; A61Q 17/04
See application file for complete search history.

(56) References Cited

U.S. PATENT DOCUMENTS

| | | | |
|---|---|---|---|
| 8,591,925 B2 | 11/2013 | Sato et al. | |
| 2002/0010245 A1* | 1/2002 | Enami | C08L 83/04 524/430 |
| 2003/0120016 A1* | 6/2003 | Okawa | C08G 77/485 528/10 |
| 2006/0204528 A1* | 9/2006 | Nolte | C09C 3/12 424/401 |
| 2008/0085966 A1 | 4/2008 | Fukui et al. | |
| 2011/0160389 A1* | 6/2011 | Bubat | C09C 1/62 524/588 |
| 2015/0272858 A1* | 10/2015 | Hayashi | A61K 47/44 424/401 |
| 2015/0274895 A1 | 10/2015 | Okawa et al. | |

FOREIGN PATENT DOCUMENTS

| | | |
|---|---|---|
| DE | 69908738 T2 | 7/2003 |
| EP | 0307098 A2 | 3/1989 |
| EP | 0825004 A1 | 2/1998 |
| EP | 1002837 B1 | 6/2003 |
| JP | H07196946 A | 8/1995 |
| JP | 2002166506 A | 6/2002 |
| JP | 2002363445 A | 12/2002 |
| JP | 2006104342 A | 4/2006 |
| JP | 2006169411 A | 6/2006 |
| JP | 2009013267 A | 1/2009 |
| JP | 2001328845 A | 11/2009 |

(Continued)

OTHER PUBLICATIONS

A Guidebook To Particle Size Analysis. Ed. Horiba Instruments Inc., 2017, 34 pages. (Year: 2017).*
Machine assisted translation of JPH07196946A obtained from https://worldwide.espacenet.com on Mar. 5, 2019, 16 pages.
Machine assisted translation of JP2002166506A obtained from https://worldwide.espacenet.com on Mar. 5, 2019, 15 pages.
Machine assisted translation of JP2002363445A obtained from https://worldwide.espacenet.com on Mar. 5, 2019, 41 pages.
Machine assisted translation of JP2006104342A obtained from https://worldwide.espacenet.com on Mar. 5, 2019, 16 pages.

(Continued)

*Primary Examiner* — Robert A Wax
*Assistant Examiner* — Olga V. Tcherkasskaya
(74) *Attorney, Agent, or Firm* — Warner Norcross + Judd LLP

(57) ABSTRACT

A treatment agent for a cosmetic powder is provided. The treatment agent contains a reactive organosiloxane represented by the following general formula (1) as a main ingredient:

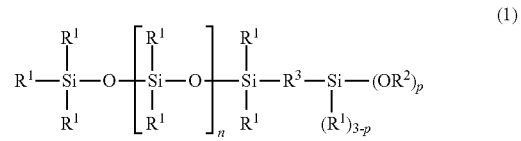

In general formula (1): each $R^1$ is independently an alkyl group having 1 to 30 carbon atoms; each $R^2$ is independently an alkyl group having 1 to 20 carbon atoms; $R^3$ is a divalent alkylene group; n is an integer of 1 to 200; and p is an integer of 1 to 3. The treatment agent for a cosmetic powder of this disclosure is capable of imparting excellent lipophilicity. A cosmetic raw material having cosmetic effect and giving an excellent feeling of use, and a cosmetic are also provided.

20 Claims, No Drawings

(56) References Cited

FOREIGN PATENT DOCUMENTS

| JP | 2010241732 A  | 10/2010 |
| JP | 2011213800 A  | 10/2011 |
| JP | 2008297397 A  | 10/2012 |
| JP | 2014077117 A  |  5/2014 |
| WO | 2014026877 A1 |  2/2014 |

OTHER PUBLICATIONS

Machine assisted translation of JP2009013267A obtained from https://worldwide.espacenet.com on Mar. 5, 2019, 3 pages.
Machine assisted translation of JP2011213800A obtained from https://worldwide.espacenet.com on Mar. 5, 2019, 3 pages.
English Translation of International Search Report for Appl. No. PCT/JP2017/022734 dated Aug. 15, 2017, 2 pages.
Machine assisted English translation of DE69908738T2 obtained from patents.google.com on Jan. 24, 2020, 10 pages.
Machine assisted English translation of JP2001328845A obtained from patents.google.com on Jan. 24, 2020, 9 pages.
Machine assisted English translation of JP2008297397A obtained from patents.google.com on Jan. 24, 2020, 11 pages.
Machine assisted English translation of WO2014026877A1 obtained from patents.google.com on Jan. 24, 2020, 27 pages.

\* cited by examiner

AGENT FOR TREATING POWDER FOR COSMETIC, POWDER FOR COSMETIC, AND COSMETIC FORMULATED USING SAID POWDER

CROSS-REFERENCE TO RELATED APPLICATIONS

This application is the National Stage of International Application No. PCT/JP2017/022734 filed on 20 Jun. 2017, which claims priority to and all advantages of Japanese Patent Appl. No. 2016-125665 filed on 24 Jun. 2016, the content of which is hereby incorporated by reference.

TECHNICAL FIELD

The present invention relates to a novel treatment agent for cosmetic powder, a cosmetic powder surface-treated with the treatment agent, and a cosmetic containing the powder.

BACKGROUND ART

By surface treating the organic particles and the inorganic particles using the powder treatment agent, new properties have been given to these particles. For example, in cosmetics, it has been increasing compatibility with cosmetic oil components, improving adhesion to the skin and increasing ultraviolet scattering effect.

By surface treating a cosmetic raw material using methylhydrogenpolysiloxane as a powder treatment agent, hydrogen remains in cosmetics and extender pigments, and from the danger in the manufacturing process due to hydrogen generation, aggregation of silicone components and the like have been mentioned as problems. As a solution, reactive alkylpolysiloxanes and the like have been developed. (JP 07-196946 A)

However, its powder treatment effect and usability were still not sufficient to obtain sufficient effect. Therefore, this solution has been sought by using an organohydrogenpolysiloxane having increased reactivity of an SiH group. (JP 2002-363445 A, JP 2009-013267 A)

Despite such technological improvement, the problem in the presence of the SiH group has been reduced but still existing, and therefore, powders specialized for lipophilically surface-treated powder have also been developed. (JP 2010-241732 A) However, there is still a problem in compatibility with other cosmetic raw materials and feeling of use.

PRIOR ART DOCUMENTS

Patent Documents

Patent Document 1: JP 07-196946 A
Patent Document 2: JP 2002-363445 A
Patent Document 3: JP 2009-013267 A
Patent Document 4: JP 2010-241732 A

SUMMARY OF THE INVENTION

Problems to be Solved by the Invention

As one aspect of the present invention, there is provided a treatment agent for a cosmetic powder capable of imparting excellent lipophilicity. As one aspect of the present invention, there is provided a cosmetic powder, a cosmetic raw material, or a cosmetic using the same, which has a cosmetic effect and has an excellent feeling of use by including the treatment agent or being treated by the treatment agent.

Means for Solving the Problems

A treatment agent for a cosmetic powder of the present invention is characterized in that it contains a reactive organosiloxane represented by the following general formula (1) as a main ingredient:

Formula 1

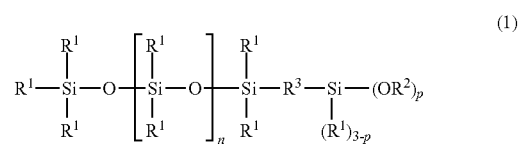

wherein each $R^1$ is independently an alkyl group having 1 to 30 carbon atoms; each $R^2$ is independently an alkyl group having 1 to 20 carbon atoms; $R^3$ is a divalent alkylene group; n is an integer of 1 to 200; and p is an integer of 1 to 3.

One of the cosmetic powders of the present invention is characterized by comprising the cosmetic powder surface-treated with the above-mentioned treatment agent. One of the cosmetic raw materials of the present invention is characterized by comprising a cosmetic powder. Further, one of the cosmetics of the present invention is characterized by comprising the above-mentioned cosmetic powder.

Effects of the Invention

The treatment agent for the cosmetic powder of the present invention can impart lipophilicity, compatibility, and dispersibility to the powder relatively easily without leaving SiH bonds in the powder. Therefore, the cosmetic powder of the present invention has not only high lipophilicity, compatibility, and dispersibility, but also high storage stability and easy handling. In addition, the cosmetic powder of the present invention has good dispersibility in cosmetics, is excellent in stability over time, and can give smooth feeling of use to the skin. The cosmetics of the present invention has the above-mentioned effects.

MODE FOR CARRYING OUT THE INVENTION

One aspect of the present invention is a treatment agent for a cosmetic powder containing a reactive organosiloxane represented by the following general formula (1) as a main ingredient:

Formula 1

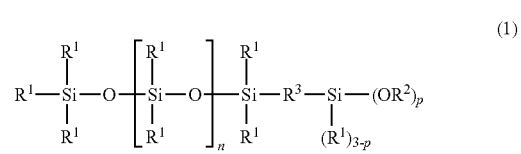

wherein each $R^1$ is independently an alkyl group having 1 to 30 carbon atoms; each $R^2$ is independently an alkyl group having 1 to 20 carbon atoms; $R^3$ is a divalent alkylene group; n is an integer of 1 to 200; and p is an integer of 1 to 3.

Examples of the $R^1$ in the formula (1) include alkyl groups such as a methyl group, an ethyl group, a propyl group, a butyl group, a pentyl group, a hexyl group, a heptyl group, an octyl group, a nonyl group, a decyl group, a lauryl group, a cetyl group, a stearyl group, and a behenyl group; and cycloalkyl groups such as a cyclopentyl group and a cyclohexyl group. Preferably, $R^1$ is a methyl group or an octyl group, or a methyl group or an octyl group for the $R^1$ at the terminal and a methyl group for the $R^1$ other than at the terminal.

$R^2$ in Formula (1) is an alkyl group having 1 to 20 carbons. Preferably, $R^2$ is an alkyl group having 1 to 12 carbon atoms, an alkyl group having 1 to 8 carbon atoms, an alkyl group having 1 to 4 carbon atoms, or a methyl group, or an ethyl group.

$R^3$ in the formula (1) is a divalent alkylene group. Preferably, $R^3$ is an alkylene group having 3 to 18 carbon atoms, an alkylene group having 4 to 15 carbon atoms, or an alkylene group having 6 to 13 carbon atoms, from the viewpoint of compatibility with oil agents used in cosmetics of the cosmetic powders. $R^3$ may be linear, or may be partially branched or cyclic.

In the formula (1), n is an integer of 1 to 200. Preferably, n is 5 or more, 10 or more, and n is 160 or less, 120 or less, 100 or less, or 80 or less, from the viewpoint of compatibility with silicone oil agents used in cosmetics of the cosmetic powders.

The number average molecular weight of the reactive organosiloxane represented by the formula (1) is suitably selected to be 300 to 100,000, or 1,000 to 10,000, although it differs depending on the powder to be treated.

The treatment agent of the cosmetic powder of the present invention contains a reactive organosiloxane represented by the general formula (1) as a main ingredient, and the content ratio thereof may be any amount capable of exhibiting an effect as a treatment agent. Preferably, the content of the organosiloxane in the treatment agent is 1 mass % or more, 5 mass % or more, 10 mass % or more, 15 mass % or more, 20 mass % or more, or 25 mass % or more. The treatment agent may be used when a reactive organosiloxane represented by the general formula (1) is used alone or also in combination with one or more other components.

Powder Surface Treating Method

The powder treatment using the treatment agent of the cosmetic powder of the present invention can be performed by a known method such as a wet method or a dry method. For example, the following methods can be cited.

1. A method of mixing a powder with a treatment agent, and then surface treating the powder using a pulverizer such as a ball mill or a jet mill.
2. A method of mixing a treatment agent with a solvent, dispersing a powder in the mixture, and then drying the solvent for surface treatment.
3. A method of adding a powder treatment agent directly or in the form of an emulsion into the aqueous slurry of the target powder, adsorbing on the surface, and then drying for surface treatment.

In addition, a method is such that after surface treating the powder, the powder is passed through a jet mill. As a method of surface treating the powder, and then passing the powder through the jet mill, for example, the following two methods can be cited. (1) A method in which a surface treatment agent and powder are mixed and dispersed by a dry process or a wet process, and then heated and dried by passing through a jet mill; and (2) a method in which the surface treatment agent and the powder are mixed and dispersed by a dry process or a wet process, followed by being heated and dried, and then passed through a jet mill. In the case of coating a powder having a primary particle diameter of submicron or more, a pulverizer such as a pin mill or a hammer mill can be used instead of the jet mill.

Examples of the mixing and dispersing machine used for mixing and contacting the above powder include a Henschel mixer, a ribbon blender, a Q mill, a kneader, a planetary mixer, a pony mixer, a Banbury mixer, a ball mill, a dry sand mill, a wet sand mill, an attritor, a disper mixer, a homomixer, an extruder, and the like. Further, at the time of this surface treatment, the surface may be treated while giving energy such as mechanochemical mechanical force, ultrasonic wave, plasma, flame, ultraviolet, electron beam, superheated steam, or the like.

The amount of the treatment agent used for the untreated cosmetic powder is preferably 0.1 to 30 parts by mass of the treatment agent with respect to 100 parts by mass of the untreated cosmetic powder. This amount ratio is preferably 1 to 20 parts by mass of the treatment agent with respect to 100 parts by mass of the cosmetic powder. Although it varies depending on the type of the cosmetic powder, the primary particle diameter, the specific surface area, the oil absorption amount, and the like, if these ratios are exceeded, the ease of dispersibility tends to be inferior.

The powder which was surface-treated by the mixing and dispersing machine is dried, for example, at a temperature of 100° C. to 170° C. for 3 hours to 20 hours in order to complete the reaction between the treating agent and the surface of the powder particles.

As a particularly preferable mode of the present description, ease of dispersibility is further improved by grinding the surface-treated powder using a jet mill pulverizer after mixing and bringing the powder into contact with each other. The jet mill is roughly classified into a fluidized bed type, a spiral type, a jet-o-mizer type, and the like, and any type of jet mill can be used, but a fluidized bed type capable of uniformly and efficiently processing is most preferable.

The particle diameter of the cosmetic powder of the present invention is represented by a median diameter, and the value thereof is preferably 0.50 μm or less, preferably 0.40 μm or less, or 0.30 μm or less. The particle diameter corresponding to 50% of the cumulative distribution is represented by D50, D84 represents the particle diameter at the point where the cumulative curve is 84%, and D16 represents the particle diameter at the point where the cumulative curve is 16%. The standard deviation (SD) of the particle diameter is measured by SD=(D84−D16)/2 using a value which is a measure of the distribution width of the particle size distribution measured by a particle size analyzer in the dynamic light scattering method. This value is preferably 0.25 μm or less, preferably 0.20 μm or less, or 0.15 μm or less.

As the cosmetic powder which can be surface-treated with the treatment agent of the present invention, any powder can be used as long as it is used in a usual cosmetic, regardless of its shape (spherical, acicular, plate-like, or the like), particle diameter (aerosol, fine particle, pigment class, or the like), particle structure (porous, non-porous, or the like). Such cosmetic powders include inorganic powders, organic powders, surfactant metal salt powders, colored pigments, pearl pigments, metal powder pigments, extender pigments, natural pigments, and the like.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, magnesia mica, lepidolite, biotite, lithia mica, silicic acid, anhydrous silicic acid, aluminum silicate, magnesium silicate, magnesium aluminum silicate, calcium silicate, barium silicate, strontium silicate, metal tungstate, hydroxyapatite, vermiculite, Higilite, bentonite, montmorillonite, hectorite, zeolite, ceramics powder, dicalcium phosphate, alumina, aluminum hydroxide, boron nitride, boron nitride, silica and the like.

Examples of the organic powder include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder, nylon 12, nylon 6, crosslinked silicone fine powder in which dimethylsilicone is crosslinked, fine powder of polymethylsilsesquioxane, styrene-acrylic acid copolymer, divinylbenzene-styrene copolymer, vinyl resin, urea resin, phenol resin, fluorine resin, silicon resin, acrylic resin, melamine resin, epoxy resin, polycarbonate resin, microcrystalline fiber powder, starch powder, lauroyl lysine, and the like.

Examples of the surfactant metal salt powder (metal soap) include zinc stearate, aluminum stearate, calcium stearate, magnesium stearate, zinc myristate, magnesium myristate, zinc cetyl phosphate, calcium cetyl phosphate, sodium zinc cetyl phosphate, and the like. Specific examples of the color pigment include inorganic red pigments such as iron oxide, iron hydroxide and iron titanate; inorganic brown pigments such as γ-iron oxide; inorganic yellow pigments such as yellow iron oxide and yellow ocher; inorganic black pigments such as black iron oxide and carbon black; inorganic violet pigments such as manganese violet and cobalt violet; inorganic green pigments such as chromium hydroxide, chromium oxide, cobalt oxide and cobalt titanate; inorganic blue pigments such as prussian blue and ultramarine blue; laked tar-based pigment, laked natural pigment, and synthetic resin powder obtained by combining these powder, and the like.

Examples of the pearl pigments include titanium oxide-coated mica, titanium oxide-coated mica, bismuth oxychloride, titanium oxide-coated bismuth oxychloride, titanium oxide-coated talc, fish scale foil, titanium oxide-coated colored mica, and the like; examples of the metal powder pigments include aluminum powder, copper powder, stainless powder, and the like; examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like; examples of the natural pigments include powders selected from carminic acid, laccaic acid, carthamin, brazillin, crocin and the like.

The cosmetic powder surface-treated with the treatment agent of the present invention, hereinafter referred to as "(A) powder", is suitable as a cosmetic raw material. The blending amount is preferably adjusted according to the type and dosage form of the cosmetic and the properties of the powder. Usually, the cosmetic powder of 0.1 to 70 mass %, typically 1 to 50 mass %, more typically 1 to 40 mass % with respect to the total mass of the cosmetic is blended.

The treatment amount of the untreated cosmetic powder and the treatment agent is preferably 0.1 to 30 parts by mass of the treatment agent with respect to 100 parts by mass of the cosmetic powder. The blending ratio is preferably 1 to 20 parts by mass of the treatment agent with respect to 100 parts by mass of the cosmetic powder. Although it varies depending on the type of the cosmetic powder, the primary particle diameter, the specific surface area, the oil absorption amount, and the like, if these ratios are exceeded, the ease of dispersibility tends to be inferior.

The cosmetic raw material of the present invention may be in the form of a liquid dispersion (slurry). The liquid dispersion includes a liquid dispersion obtained by dispersing the cosmetic powder after treatment with a cosmetic powder treatment agent in an oil agent, or a liquid dispersion obtained by dissolving or dispersing organosiloxane in an oil agent, adding powders thereto and mixing and dispersing the same. The content of the cosmetic powder and the oil agent in the cosmetic raw material is preferably 10 to 5,000 parts by mass with respect to 100 parts by mass of the cosmetic powder after treatment. The content of the oil agent is preferably 30 parts by mass or more, 50 parts by mass or more, 100 parts by mass or more, 200 parts by mass or more, 5,000 parts by mass or less, 3,000 parts by mass or less, 2,000 parts by mass or less, or 1,000 parts by mass or less with respect to 100 parts by mass of the cosmetic powder.

The above-mentioned oil agent is not particularly limited as long as it can prepare a liquid dispersion, and is generally used as a component of a cosmetic, and is usually liquid at room temperature, but may be a solid such as wax, or may be a gum or paste having a high viscosity and viscous, which will be described later. Such an oil agent is suitably one or more oil agents selected from silicone oils, non-polar organic compounds or low polarity organic compounds which are liquid at 5 to 100° C.

In the cosmetic of the present invention, one or more of "(B) oil agents" can be used depending on the purpose. Any oil agent, in the form of solid, semi-solid or liquid, can be used as long as it is used in ordinary cosmetics.

For example, natural animal and vegetable oils and fats and semi-synthetic oils and fats include avocado oil, linseed oil, almond oil, insects wax, *perilla* oil, olive oil, cocoa butter, kapok wax, kaya oil, carnauba wax, liver oil, candelilla wax, beef tallow, beef foot oil, beef bone fat, hardened beef tallow, apricot kernel oil, whale wax, hydrogenated oil, wheat germ oil, sesame oil, rice germ oil, rice bran oil, sugar cane wax, *camellia* kissi seed oil, safflower oil, shea butter, Chinese tung oil, cinnamon oil, jojoba wax, shellac wax, turtle oil, soybean oil, tea seed oil, *camellia* oil, evening primrose oil, corn oil, lard, rapeseed oil, Japanese tung oil, bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, Macadamia nut oil, beeswax, mink oil, cottonseed oil, cotton wax, Japan wax, Japan wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, yolk oil, and the like, wherein POE stands for polyoxyethylene.

Hydrocarbon oils include ozokerite, squalane, squalene, ceresin, paraffin, paraffin wax, liquid paraffin, pristane, polyisobutylene, microcrystalline wax, vaseline, and the like; and higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, and the like.

Higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecanol, cholesterol, phytosterol, POE cholesterol ether, monostearyl glycerine ether (batyl alcohol), monooleyl glyceryl ether (ceralkyl alcohol), and the like.

Ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl-2-ethylhexanoate, tri-2-ethylhexanoate trimethylolpropane, tetra-2-ethylhexanoate pentaerythritol, cetyl octanoate, octyl dodecyl gum ester, oleyl oleate, octyl dodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl cebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyl octanoate, ethyl laurate, hexyl laurate, N-lauroyl-L-glutamic acid-2-octyldodecyl ester, diisostearyl malate, and the like; glyceride oils include acetoglyceryl, glyceryl triisooctanoate, glyceryl triisostearate, glyceryl triisopalmitate, glyceryl monostearate, glyceryl di-2-heptylundecanoate, glyceryl trimyristate, diglyceryl myristate isostearate, and the like.

Examples of silicone oils include low viscosity to high viscosity organopolysiloxanes such as dimethylpolysiloxane, methylphenylpolysiloxane, methylhydrogenpolysiloxane, dimethylsiloxane/methylphenylsiloxane copolymer; cyclic siloxanes such as octamethylcyclotetrasiloxane, decamethylcyclopentasiloxane, dodecamethylcyclohexasiloxane, tetramethyltetrahydrogen cyclotetrasiloxane, tetramethyltetraphenylcyclotetrasiloxane; silicone rubber such as gum-like dimethylpolysiloxane having a high degree of polymerization, gum-like dimethylsiloxane-methylphenylsiloxane copolymer; and higher alkoxy-modified silicones such as cyclic siloxane solution of silicone rubber, trimethylsiloxysilicate, cyclic siloxane solution of trimethylsiloxysilicate, stearoxysilicone; higher fatty acid-modified silicones, alkyl-modified silicones, amino-modified silicones, fluorine-modified silicones, silicone resins and a solution of silicone resins, and the like. Examples of the fluorine-based oil agents include perfluoropolyether, perfluorodecalin, perfluorooctane, and the like.

The blending amount of these oil agents (B) is 1 to 98 mass %, preferably 2 to 50 mass % of the total cosmetic, although it differs depending on the agent system.

In the cosmetic of the present invention, "(C) water" can be blended depending on the purpose. The blending amount is 1 to 95 mass %, preferably 5 to 80 mass % of the total cosmetic, although it differs depending on the agent system.

In the cosmetic of the present invention, one or more of "(D) surfactants" can be used depending on the purpose. Such surfactants include anionic, cationic, nonionic and amphoteric surfactants.

Examples of the anionic surfactants include fatty acid soaps such as sodium stearate and triethanolamine palmitate, alkyl ether carboxylic acids and salts thereof, condensate salts of amino acids and fatty acids, alkane sulfonates, alkene sulfonates, sulfonates of fatty acid esters, sulfonates of fatty acid amides, formalin condensate sulfonates, alkyl sulfates, secondary higher alcohol sulfates, alkyl and allyl ether sulfates, sulfates of fatty acid ester, sulfates of fatty acid alkylamides, sulfates such as turkey red oil, alkyl phosphates, ether phosphates, alkyl allyl ether phosphates, amide phosphates, N-acyl amino acid-based active agents; examples of the cationic surfactants include amine salts such as alkylamine salts, polyamine and amino alcohol fatty acid derivatives, alkyl quaternary ammonium salts, aromatic quaternary ammonium salts, pyridium salts, imidazolium salts, and the like.

Non-ionic surfactants include sorbitan fatty acid esters, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkyl phenyl ether, polyoxyethylene fatty acid ester, poly oxyethylene sorbitan fatty acid ester, polyoxyethylene sorbitol fatty acid ester, polyoxyethylene glycerin fatty acid ester, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched polyoxyalkylene modified organopolysiloxane, linear or branched polyoxyalkylene-modified organopolysiloxane, linear or branched polyoxyalkylene-alkyl co-modified organopolysiloxane, alkanolamide, sugar ether, sugar amide, and the like.

Examples of the amphoteric surfactant include betaine, an aminocarboxylate, an imidazoline derivative, an amidoamine type, and the like.

Among these surfactants, generally, in view of the tendency to provide stable 0/W type emulsions, anionic surfactants such as fatty acid soaps such as sodium stearate or triethanolamine palmitate, alkyl sulfates, alkyl phosphates, alkyl quaternary ammonium salts, and the like; and nonionic surfactants such as sorbitan fatty acid esters, glycerin fatty acid esters, polyoxyethylene sorbitan fatty acid esters, polyoxyethylene hydrogenated castor oils, linear or branched polyoxyalkylene-modified organopolysiloxanes, linear or branched polyoxyalkylene-alkyl co-modified organopolysiloxanes, and particularly nonionic surfactants having HLB of 2 to 8 are preferable. In addition, linear or branched silicones having a polyoxyalkylene chain and a polyglycerin chain is generally preferable for a W/0 type cosmetic.

The blending amount of the surfactant is in the range of 0.1 to 20 mass %, particularly preferably 0.2 to 10 mass % of the total cosmetic.

In the cosmetic of the present invention, one or more of "(E) a compound having an alcoholic hydroxyl group" can be used depending on the purpose.

Compounds having an alcoholic hydroxyl group which can be added in the present invention include lower alcohols such as ethanol and isopropanol, sugar alcohols such as sorbitol and maltose, and sterols such as cholesterol, sitosterol, phytosterol and lanosterol, polyhydric alcohols such as butylene glycol, propylene glycol and dibutylene glycol, and the like. The blending amount is preferably in the range of 0.1 to 98 mass % of the total cosmetic.

In the cosmetic of the present invention, one or more of "(F) water-soluble or water-swellable polymer" can be used depending on the purpose.

For example, vegetable-based polymers such as gum arabic, tragacanth, galactan, carob gum, guar gum, karaya gum, carrageenan, pectin, agar, quince seed (marmelo), starch (rice, corn, potato, wheat), algae colloid, trant gum, and locust bean gum; microorganism-based polymers such as xanthan gum, dextran, succinoglycan, and pullulan; animal-based polymers such as collagen, casein, albumin, and gelatin; starch-based polymers such as carboxymethyl starch and methylhydroxypropyl starch; cellulose-based polymers of cellulose powder such as methyl cellulose, ethyl cellulose, methylhydroxypropylcellulose, carboxymethylcellulose, hydroxymethylcellulose, hydroxypropylcellulose, nitrocellulose, sodium cellulose sulfate, sodium carboxymethylcellulose, crystalline cellulose; alginic acid-based polymers such as sodium alginate and alginic acid propylene glycol esters; vinyl-based polymers such as polyvinylmethyl ether and carboxyvinyl polymer; polyoxyethylene-based polymers; polyoxyethylene polyoxypropylene copolymer-based polymers; acrylic polymers such as sodium polyacrylate, polyethylacrylate, polyacrylamide; other synthetic water-soluble polymers such as polyethyleneimine and cationic polymers; inorganic water-soluble polymers such as bentonite, aluminum magnesium silicate, montmorillonite, biderite, nontronite, saponite, hectorite, and anhydrous silicic acid; and the like. These water-soluble polymers also include film forming agents such as polyvinyl alcohol and polyvinyl pyrrolidone. The blending amount is preferably in the range of 0.1 to 25 mass % of the total cosmetic.

Also, in the cosmetic of the present invention, at least one silicone resin selected from acrylic silicone resin and network silicone resin can be used according to the purpose. The acrylic silicone resin may be either an acrylic/silicone graft polymer or an acrylic/silicone block copolymer. However, these network silicone resins do not have SiH bonds. Preferably, the acrylic silicone resin and the network silicone resin have at least one selected from a pyrrolidone moiety, a long chain alkyl moiety, a polyoxyalkylene moiety and a fluoroalkyl moiety, a carboxylic acid, and an amino group. The acrylic silicone resin and the network silicone resin are preferably 0.1 to 20 mass %, more preferably 1 to 10 mass % with respect to the total amount of the cosmetic.

Further, to the cosmetic of the present invention, components commonly used in cosmetics such as oil-soluble gelling agents, organic modified clay minerals, resins, antiperspirants, ultraviolet absorbing agents, ultraviolet absorbing/scattering agents, moisturizing agents, antiseptic agents, antibacterial agents, perfumes, salts, antioxidants, pH adjusting agents, chelating agents, refreshing agents, anti-inflammatory agents, ingredients for a beautiful skin (such as skin-whitening agents, cell activators, skin roughening ameliorating agents, blood circulation promotors, skin astringents, antiseborrheic agents), vitamins, amino acids, nucleic acids, hormones, clathrate compounds, hair fixing agents, and the like, can be added within a range that does not prevent the effect of the present invention.

Oil-soluble gelling agents include gelling agents selected from metal soaps such as aluminum stearate, magnesium stearate, and zinc myristate; amino acid derivatives such as N-lauroyl-L-glutamic acid, and α,γ-di-n-butylamine; dextrin fatty acid esters such as dextrin palmitate, dextrin stearate, and dextrin 2-ethylhexanoate palmitate; sucrose fatty acid esters such as sucrose palmitate and sucrose stearate; benzylidene derivatives of sorbitol such as monobenzylidenesorbitol and dibenzylidenesorbitol; organically modified clay minerals such as dimethylbenzyldodecylammonium montmorillonite clay, and dimethyldioctadecylammonium montmorillonite clay; and the like.

Examples of the antiperspirants include antiperspirants selected from aluminum chlorohydrate, aluminum chloride, aluminum sesquichlorohydrate, zirconyl hydroxychloride, aluminum zirconium hydroxychloride, aluminum zirconium glycine complex, and the like.

Ultraviolet absorbing agents include benzoic acid-based ultraviolet absorbing agents such as paraaminobenzoic acid, anthranilic acid-based ultraviolet absorbing agents such as methyl anthranilate, salicylic acid-based ultraviolet absorbing agents such as methyl salicylate, silicic acid-based ultraviolet absorbing agents such as paramethoxysilicic acid octyl, benzophenone-based ultraviolet absorbing agents such as 2,4-dihydroxybenzophenone, urocanic acid-based ultraviolet absorbing agents such as ethyl urocaninate, and dibenzoylmethane-based ultraviolet absorbing agents such as 4-t-butyl-4'-methoxy-dibenzoylmethane, and the like. Ultraviolet absorbing/scattering agents include powder that absorbs and scatters ultraviolet such as fine particulate titanium oxide, fine particulate iron oxide-containing titanium oxide, fine particulate zinc oxide, fine particulate cerium oxide, and complexes thereof.

Moisturizing agents include glycerin, sorbitol, propylene glycol, dipropylene glycol, 1,3-butylene glycol, glucose, xylitol, maltitol, polyethylene glycol, hyaluronic acid, chondroitin sulfate, pyrrolidone carboxylate, polyoxyethylene methyl glucoside, polyoxypropylene methyl glucoside, and the like.

Antimicrobial-antiseptic agents include paraoxybenzoic acid alkyl esters, benzoic acid, sodium benzoate, sorbic acid, potassium sorbate, phenoxyethanol and the like, and antibacterial agents include benzoic acid, salicylic acid, carbolic acid, sorbic acid, paraoxybenzoic acid alkyl esters, parachlorometacresol, hexachlorophene, benzalkonium chloride, chlorhexidine chloride, trichlorocarbanilide, photosensitizer, phenoxyethanol and the like.

Antioxidants include tocopherol, butyl hydroxyanisole, dibutyl hydroxytoluene, phytic acid, and the like; pH adjusting agents include lactic acid, citric acid, glycolic acid, succinic acid, tartaric acid, dl-malic acid, potassium carbonate, sodium hydrogen carbonate, ammonium hydrogen carbonate, and the like; chelating agents include alanine, sodium edetate, sodium polyphosphate, sodium metaphosphate, phosphoric acid, and the like; refreshing agents include L-menthol, camphor, and the like; and anti-inflammatory agents include allantoin, glycyrrhetinic acid and salts thereof, glycyrrhetinic acid and stearyl glycyrrhetinate, tranexamic acid, azulene, and the like.

Ingredients for a beautiful skin include skin-whitening agents such as placental extracts, albutin, glutathione, and euquinosita extracts; cell activators such as royal jellies, photosensitive agents, cholesterol derivatives, and juvenile blood extracts; skin roughening ameliorating agents; blood circulation promotors such as noncyclic acid vanillylamine, benzyl nicotinate, β-butoxyethyl nicotinate, capsaicin, gingeron, cantharides tincture, ichthammol, caffeine, tannic acid, α-borneol, tocopherol nicotinates, inositol hexanicotinate, cyclandelate, cinnarizine, triazoline, acetylcholine, verapamil, cepharanthine, and γ-oryzanol; skin astringents such as zinc oxide and tannic acid; antiseborrheic agents such as sulfur and thianthol, and the like.

Vitamins include vitamin A such as vitamin A oil, retinol, retinol acetate, and retinol palmitate; vitamin B2 such as riboflavin, riboflavin butyrate, and flavin adenine nucleotide; Vitamin B6 such as pyridoxine hydrochloride, pyridoxine dioctanoate, and pyridoxine tripalmitate; vitamin B such as vitamin B12 and derivatives thereof, and vitamin B15 and derivatives thereof; vitamin C such as L-ascorbic acid, L-ascorbic acid dipalmitate, L-ascorbic acid-2-sodium sulfate, and L-ascorbic acid phosphate diester dipotassium; vitamin D such as ergocalciferol, and cholecalciferol; Vitamin E such as α-tocopherol, β-tocopherol, γ-tocopherol, dl-α-tocopherol acetate, dl-α-tocopherol nicotinate, and dl-α-tocopherol succinate; vitamin H; vitamin P; nicotinic acids such as nicotinic acid, benzyl nicotinate, and nicotinic acid amide; pantothenic acids such as calcium pantothenate, D-pantothenyl alcohol, pantothenyl ethyl ether, and acetyl pantothenyl ethyl ether; biotin, and the like.

Amino acids include glycine, valine, leucine, isoleucine, serine, threonine, phenylalanine, arginine, lysine, aspartic acid, glutamic acid, cysteine, cysteine, methionine, tryptophan, and the like; nucleic acids include deoxyribonucleic acid and the like; hormones include estradiol, ethinylestradiol, and the like.

Hair fixing polymeric compounds include amphoteric, anionic, cationic, and nonionic polymer compounds, and examples thereof include polyvinyl pyrrolidone polymer compounds such as polyvinyl pyrrolidone and vinyl pyrrolidone/vinyl acetate copolymer; acidic vinyl ether based polymers such as methyl vinyl ether/maleic anhydride alkyl half ester copolymer; acidic polyvinyl acetate based polymers such as vinyl acetate/crotonic acid copolymer; acidic acrylic polymer compounds such as (meth)acrylic acid/alkyl (meth)acrylate copolymer, (meth)acrylic acid/alkyl (meth)acrylate/alkylacrylamide copolymer; amphoteric acrylic polymer compounds such as N-methacryloxyethyl-N, N-dimethylammonium·α-N-methylcarboxybetaine/alkyl (meth)acrylate copolymer, hydroxypropyl (meth)acrylate/butylaminoethyl methacrylate/acrylic acid octyl amide copolymer. In addition, naturally-derived polymeric compounds such as cellulose or derivatives thereof, keratin and collagen or derivatives thereof can be suitably used.

The cosmetics of the present invention include skin care cosmetics such as lotions, milky lotions, creams, cleansing agents, packs, oil liquids, massage agents, detergents, deodorants, hand creams, and lip creams; makeup cosmetics such as makeup bases, face powder, liquid foundations, oily foundations, blushers, eye shadows, mascara, eyeliners, eyebrows, and lipsticks; hair cosmetics such as shampoos, rinses, treatments, and setting agents; antiperspirants; ultraviolet protective cosmetics such as sunscreen milk lotions, and sunscreen creams.

These cosmetics may be in various forms such as liquid, emulsion, cream, solid, paste, gel, powder, press, mousse, spray, stick, pencil, and the like.

EXAMPLES

The treatment agent of the present invention and the method for producing the same will be explained in detail by synthesis examples, examples, and comparative examples. However, the present invention is not limited to these examples. Hereinafter, simply "%" and "parts" mean mass % and parts by mass, respectively. In addition, the viscosities in Synthesis Examples, Examples, and Comparative Examples are values at 25° C.

Synthesis Example 1

To the reactor, 189 g of an organohydrogensiloxane represented by the following formula (2):

Formula 2

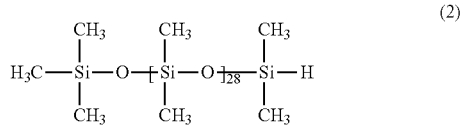

(2)

and 21.0 g of 5-hexenyltrimethoxysilane were charged and heated to 50 to 60° C. while stirring under an inert gas. After 0.1 g of a solution of platinum-1,3-divinyltetradimethyldisiloxane complex in isopropyl alcohol (platinum concentration 0.38%) was added, the reaction solution was stirred while maintaining the temperature at 85 to 95° C. Next, 0.5 g of the reaction solution was taken and it was confirmed that the reaction was completed by an alkali decomposition gas generation method (the remaining Si—H group was decomposed by KOH in an ethanol/aqueous solution, and the reaction rate was calculated from the volume of hydrogen gas generated). After the reaction solution was warmed to 150 to 160° C. under reduced pressure to remove low-boiling components such as isopropyl alcohol, 192 g of a treatment agent for a cosmetic powder containing 80% or more of reactive organosiloxane represented by the following formula (3):

Formula 3

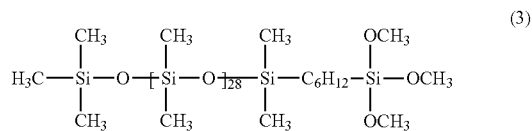

was obtained. The above Formula was confirmed by $^1$H-NMR and $^{29}$Si-NMR. The viscosity of the obtained reactive organosiloxanes was measured according to JIS-Z-8803 using an Ubbelohde-type viscosity tube and found to be 31 mm$^2$/s.

Synthesis Example 2

265 g of an organohydrogensiloxane represented by the following formula (4):

Formula 4

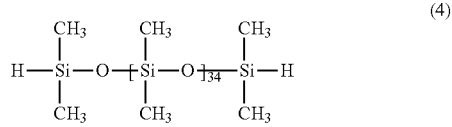

was used instead of the organohydrogensiloxane of the formula (2) in Synthesis Example 1, and 284 g of a treatment agent for a cosmetic powder containing 33.3% or more of a reactive organosiloxane represented by the following formula (5):

Formula 5

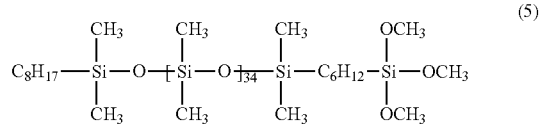

was obtained by synthesizing in the same manner as in Example 1 except that 19.8 g of 5-hexenyltrimethoxysilane and 15.5 g of 1-octene and 0.16 g of a solution of platinum-1,3-divinyltetradimethyldisiloxane complex in isopropyl alcohol (platinum concentration: 0.38%) were used. The above Formula was confirmed by $^1$H-NMR and $^{29}$Si-NMR. The viscosity of the resulting reactive organosiloxanes was measured according to JIS-Z-8803 using an Ubbelohde-type viscosity tube and found to be 51 mm$^2$/s.

Examples 1 to 2 and Comparative Example 1

To 50 g of untreated fine particle titanium oxide (STR-100N, manufactured by Sakai Chemical Industries, Ltd.) was added 50 g of n-hexane, and while stirring with a disper, a solution obtained by mixing 2.5 g of the treatment agent prepared in Synthesis Example 1 and 5 g of hexane was added dropwise, and then the mixture was further stirred with a disper for 10 minutes. Next, after 10 minutes in an ultrasonic washing machine, n-hexane was removed under normal pressure while stirring at 100° C., and further baking process was performed at 150° C. for 3 hours while stirring under reduced pressure to obtain a cosmetic powder.

Subsequently, 20 g of decamethylpentacyclosiloxane (D$_5$), 4 g of polyether-modified silicone (ES-5612 Formulation Aid, manufactured by Dow Corning Toray Co., Ltd.), 0.04 g of ion-exchange water, 16 g of resulting cosmetic powder, and 120 g of zirconia beads were ground and dispersed in a paint shaker for 15 hours to obtain a slurry-like cosmetic raw material as Example 1 containing titanium oxide treated in 5 parts of the treatment agent of Synthetic Example 1 with respect to 100 parts of untreated titanium oxide. Likewise, for Example 2, a cosmetic raw material in the form of a slurry containing titanium oxide treated in the same manner was obtained using the treatment agent of Synthesis Example 2. As Comparative Example 1, a slurry-like cosmetic raw material containing titanium oxide with the same composition was produced using a powder treated similarly with 100 parts of the same untreated titanium oxide with 5 parts of methylhydrogen polysiloxane.

Evaluation 1

For the titanium oxide slurries of Examples 1 to 2 and Comparative Example 1, the viscosity was measured with an E type viscometer (VISCONIC EMD, manufactured by Tokyo-keiki Co., Ltd.), the median diameter of the titanium oxide slurry particles (particle diameter corresponding to 50% of the cumulative distribution, D50, μm) and the standard deviation SD (the particle diameter distribution SD=(D84-D16)/2 as a measure of the distribution width of the measured particle size distribution (μm), wherein D84 represents the particle diameter (μm) of the point where the cumulative curve is 84%, and D16 represents the particle diameter (μm) of the point where the cumulative curve is 16%) were measured with a particle size analyzer (MICROTRAC UPA model 9340-UPA, manufactured by Nikkiso Co., Ltd.) using a dynamic light scattering method.

TABLE 1

| titanium oxide slurry | viscosity [mPa · s] | | particle diameter | |
|---|---|---|---|---|
| | at the time of production | after 4 months at room temperature | median diameter (D50) [μm] | standard deviation SD [μm] |
| Example 1 | 267 | 194 | 0.15 | 0.07 |
| Example 2 | 313 | 288 | 0.16 | 0.09 |
| Comparative Example 1 | 1388 | Unmeasurable due to solidification. | 0.93 | 0.46 |

As shown in Table 1, it was confirmed that the titanium oxide slurries of Examples 1 to 2 were excellent in dispersibility because of lower viscosity and smaller median diameter and/or standard deviation SD as compared with Comparative Example 1. It was confirmed that the stability over time was excellent.

Examples 3 to 4 and Comparative Example 2

To 50 g of untreated fine particle titanium oxide (STR-100N, manufactured by Sakai Chemical Industries, Ltd.) was added 50 g of n-hexane, and while stirring with a disper, a solution obtained by mixing 5 g of the powder treatment agent prepared in Synthesis Example 1 and 5 g of hexane was added dropwise, and then the mixture was further stirred with a disper for 10 minutes. Next, after 10 minutes in an ultrasonic washing machine, n-hexane was removed under normal pressure while stirring at 100° C., and further baking process was performed at 150° C. for 3 hours while stirring under reduced pressure to obtain a cosmetic powder.

Subsequently, 20 g of isohexadecane (Alamo) HD, manufactured by Croda Japan KK), 4 g of polyether-modified silicone (ES-5600 Silicone Glycerol Emulsifier, manufactured by Dow Corning Toray Co., Ltd.), 0.04 g of ion-exchange water, 16 g of resulting cosmetic powder, and 120 g of zirconia beads were ground and dispersed in a paint shaker for 15 hours to obtain a slurry-like cosmetic raw material as Example 3 containing titanium oxide treated in 10 parts of the treatment agent of Synthetic Example 1 with respect to 100 parts of untreated titanium oxide. Likewise, in Example 4, a cosmetic raw material in the form of a slurry containing titanium oxide treated in the same manner was obtained using the treatment agent of Synthesis Example 2. As Comparative Example 2, a slurry-like cosmetic raw material containing titanium oxide with the same composition was produced using fine particle titanium oxide treated with methylhydrogen polysiloxane (MTY-02, manufactured by Tayca Corporation).

Evaluation 2

Using the titanium oxide slurries of Examples 3 to 4 and Comparative Example 2, sunscreen (W/O) creams were produced according to the following formulation, and SPF values (ultraviolet protection index) and PA values (UV-A protection index) were measured.

SPF-value measuring instrument: UV-1000S (manufactured by Labsphere, Inc.)

Conditions: Three samples were prepared in which 2.00 mg/cm$^2$ of the sample was applied to a Transpore surgical tape (manufactured by 3M Japan Limited), 10 points were measured per sample, the average value was calculated by deleting the highest value and the lowest value, and using 8 measured values. The mean value of the three samples was used as the SPF value. The PA value was also measured under the same conditions using the same measuring instrument.

Component

Phase A 1) 2 parts of lauryl PEG-10 tris (trimethylsiloxy) silylethyl dimethicone (Note 1)

2) 1 part of (Diphenylmethyl siloxyphenyl methicone/phenyl silsesquioxane) cross polymer (Note 2)

3) 6 parts of caprylyl methicone (Note 3)

4) 7.5 parts of ethylhexyl methoxy cinnamic acid (Note 4)

5) 2 parts of hexyl diethylamino hydroxybenzoyl benzoate (Note 5)

6) 3 parts of phenyl trimethicone (Note 6)

7) 3 parts of isododecane, (dimethicone/bisisobutyl PPG-20) cross polymer (Note 7)

8) 0.3 parts of silica silylate (Note 8)

9) 15 parts of the titanium oxide slurry produced in Example 3, or Example 4, or Comparative

Example 2

Phase B
10) 7 parts of butylene glycol
11) 0.2 parts of sodium citrate
12) 0.5 parts of sodium chloride
13) 52.5 parts of purified water
Note 1: ES 5300 Formulation Aid, manufactured by Dow Corning Toray Co., Ltd. was used.
Note 2: PH 1560 Glossy Fluid, manufactured by Dow Corning Toray Co., Ltd. was used.
Note 3: FZ-3196, manufactured by Dow Corning Toray Co., Ltd. was used.
Note 4: Uvinul MC80, manufactured by BASF Japan Ltd. was used.
Note 5: Uvinul A Plus, manufactured by BASF Japan Ltd. was used.
Note 6: SH556 Fluid, manufactured by Dow Corning Toray Co., Ltd. was used.
Note 7: EL-8050 ID Silicone Organic Elastomer Blend, manufactured by Dow Corning Toray Co., Ltd. was used.
Note 8: VM-2270 Aerogel Fine Particle, manufactured by Dow Corning Toray Co., Ltd. was used.
Procedure
1. Components 1 to 9 are stirred with a disper to obtain the reactants.
2. Components 10 to 13 are mixed to obtain a mixture.
3. The mixture obtained in step 2 is added to the reaction obtained in step 1 and emulsified.
Evaluation Method for Feeling of Use
Evaluation of feeling of use was also carried out by the following method. Based on ten professional evaluation panels, evaluation of spreadability at the time of application to the skin and smoothness after drying were evaluated in 5 grades according to the following criteria, and further judged from the average score.
Evaluation
5: Very good
4: Good
3: Normal
2: Not very good
1: Not good
◎: Average score 4.5 or more
○: Average score 3.5 or more and less than 4.5
Δ: Average score 2.5 or more and less than 3.5
x: Average score less than 2.5
The evaluation results are shown in Table 2.

TABLE 2

| titanium oxide slurry | SPF value | PA value | spreadability | smoothness |
|---|---|---|---|---|
| Example 3 | 34 | +++ | ◎ | ◎ |
| Example 4 | 41 | +++ | ◎ | ◎ |
| Comparative Example 2 | 21 | ++ | Δ | ○ |

As can be seen from Table 2, it was confirmed that the SPF value and the PA value of Examples 3 to 4 were superior to those of the conventional product of Comparative Example 2, and it was also confirmed that they were excellent also in feeling of use.

INDUSTRIAL APPLICABILITY

By using the treatment agent of the present invention, the lipophilicity of the cosmetic powder can be effectively enhanced. The cosmetic powder treated with this treatment agent is characterized by high lipophilicity. In addition, the cosmetic having the cosmetic powder has a feature of having a good tactile impression. Further, the treatment agent obtained in this manner can be used not only as a cosmetic but also as a treatment agent widely used in various fields such as plastic additives, inks, paints, toners (magnetic powders), chemical fibers, packaging materials, and the like.

The invention claimed is:

1. A cosmetic powder surface-treated with a treatment agent, the treatment agent comprising an organosiloxane represented by the following general formula (1') as a main ingredient:

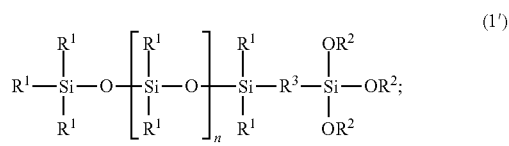

wherein each $R^1$ is independently an alkyl group having 1 to 30 carbon atoms; each $R^2$ is independently an alkyl group having 1 to 20 carbon atoms; $R^3$ is a divalent alkylene group having 6 to 18 carbon atoms; and subscript n is an integer of from 1 to 200; and wherein the cosmetic powder particle median diameter is 0.50 µm or less as measured using a dynamic light scattering method.

2. The cosmetic powder according to claim 1, wherein $R^3$ is a divalent alkylene group having 6 to 13 carbon atoms.

3. The cosmetic powder according to claim 1, wherein the cosmetic powder particle median diameter is 0.40 µm or less as measured using a dynamic light scattering method.

4. The cosmetic powder according to claim 3, wherein the cosmetic powder particle median diameter is 0.30 µm or less as measured using a dynamic light scattering method.

5. The cosmetic powder according to claim 1, wherein the standard deviation of the cosmetic powder particle median diameter is 0.25 µm or less.

6. A cosmetic raw material comprising 10 to 10,000 parts by mass of the cosmetic powder according to claim 1 and an oil agent, with respect to 100 parts by mass of the cosmetic powder.

7. A cosmetic blended with the cosmetic powder according to claim 1.

8. The A cosmetic powder according to claim 2, wherein $R^3$ is $-[CH_2]_6-$.

9. The cosmetic powder according to claim 5, wherein the standard deviation of the cosmetic powder particle median diameter is 0.20 µm or less.

10. The cosmetic powder according to claim 9, wherein the standard deviation of the cosmetic powder particle median diameter is 0.15 µm or less.

11. A cosmetic raw material comprising 10 to 10,000 parts by mass of the cosmetic powder according to claim 10 and an oil agent, with respect to 100 parts by mass of the cosmetic powder.

12. A cosmetic blended with the cosmetic powder according to claim 10.

13. The cosmetic powder according to claim 1, wherein each $R^1$ is independently a methyl group or an octyl group.

14. The cosmetic powder according to claim 13, wherein each $R^1$ is a methyl group.

15. The cosmetic powder according to claim 13, wherein $R^1$ is an octyl group at the terminal location and a methyl group for the other locations.

16. The cosmetic powder according to claim 1, wherein each $R^2$ is independently a methyl group or an ethyl group.

17. The cosmetic powder according to claim 1, wherein each $R^2$ is a methyl group.

18. The cosmetic powder according to claim 1, wherein subscript n is an integer of from 5 to 80.

19. A cosmetic raw material comprising 10 to 5,000 parts by mass of the cosmetic powder according to claim 3 and an oil agent, with respect to 100 parts by mass of the cosmetic powder.

20. A cosmetic raw material comprising 10 to 5,000 parts by mass of the cosmetic powder according to claim 10 and an oil agent, with respect to 100 parts by mass of the cosmetic powder.

* * * * *